United States Patent [19]
Phillips

[11] Patent Number: 5,776,205
[45] Date of Patent: *Jul. 7, 1998

[54] SPLIT FOOT PROSTHESIS

[76] Inventor: Van L. Phillips, 5499 Avenida Maravillas, Rancho Santa Fe, Calif. 92067

[*] Notice: The term of this patent shall not extend beyond the expiration date of Pat. No. 5,181,933.

[21] Appl. No.: 789,159

[22] Filed: Jan. 24, 1997

Related U.S. Application Data

[63] Continuation of Ser. No. 643,869, May 7, 1996, abandoned, which is a continuation of Ser. No. 185,325, Jan. 21, 1994, Pat. No. 5,514,185, which is a continuation of Ser. No. 91,458, Jul. 14, 1993, abandoned, which is a continuation of Ser. No. 936,854, Aug. 27, 1992, abandoned, which is a continuation of Ser. No. 662,928, Feb. 28, 1991, Pat. No. 5,181,933.

[51] Int. Cl.⁶ .................................................. A61F 2/66
[52] U.S. Cl. ..................................... 623/55; 623/52
[58] Field of Search ................................. 623/47-56

[56] References Cited

U.S. PATENT DOCUMENTS

| | | | |
|---|---|---|---|
| 61,780 | 2/1867 | Watson | 623/38 |
| 65,187 | 5/1867 | Emery . | |
| 546,405 | 9/1895 | Marks et al. | 623/55 |
| 951,989 | 3/1910 | Hanger . | |
| 961,582 | 6/1910 | Bradley et al. | 623/52 |
| 1,424,264 | 8/1922 | Shrodes . | |
| 1,502,593 | 7/1924 | Shrodes . | |
| 1,804,915 | 5/1931 | Collins . | |
| 2,036,830 | 4/1936 | Rowley . | |
| 2,197,093 | 4/1940 | Campbell . | |
| 2,440,075 | 4/1948 | Campbell . | |
| 2,453,969 | 11/1948 | Carter . | |
| 2,475,372 | 7/1949 | Catranis . | |
| 3,754,286 | 8/1973 | Ryan . | |
| 4,547,913 | 10/1985 | Phillips . | |
| 4,645,509 | 2/1987 | Poggi et al. . | |
| 4,676,801 | 6/1987 | Landeen . | |
| 4,721,510 | 1/1988 | Cooper et al. . | |
| 4,822,363 | 4/1989 | Phillips . | |
| 4,892,554 | 1/1990 | Robinson . | |
| 4,938,776 | 7/1990 | Masinter . | |
| 5,181,933 | 1/1993 | Phillips | 623/55 |

FOREIGN PATENT DOCUMENTS

| | | |
|---|---|---|
| 325171 | 9/1920 | Germany . |
| 883321 | 7/1953 | Germany . |
| 963849 | 5/1957 | Germany . |
| 1498490 | 11/1987 | U.S.S.R. . |
| 306313 | 2/1929 | United Kingdom . |

OTHER PUBLICATIONS

"The Seattle prosthesis Foot–A Design for Active Sports: Preliminary Studies," E.M. Burgess, M.D., et al., *Orthotics and prosthetics Journal*, vol. 37, No. 1, Spring 1983.
The Seattle Foot—Winner of Presidential Design Award—Jan. 20, 1985.
L.A. *Times* View Section, "Seattle Foot," Jun. 12, 1984.

*Primary Examiner*—David H. Willse
*Attorney, Agent, or Firm*—Knobbe, Martens, Olson & Bear LLP

[57] ABSTRACT

A prosthetic foot is characterized by an attachment section and plurality of curvilinear foot portions extending downwardly from the attachment section to contact a supporting surface. The portions are capable of movement independent from one another. Preferably, the plurality of foot portions is fabricated by dividing a forefoot portion and a heel portion demountably attached thereto. Such division may be achieved by the provision of a slot in said forefoot and heel portions. A strap or similar expedient is provided to limit the movement of the foot portions relative to each other.

34 Claims, 3 Drawing Sheets

SPLIT FOOT PROSTHESIS

This application is a continuation of U.S. patent application Ser. No. 08/643,869, filed May 7, 1996, now abandoned, which was a continuation of U.S. patent application Ser. No. 08/185,325, filed Jan. 21, 1994, now U.S. Pat. No. 5,514,185, which was a continuation of U.S. patent application Ser. No. 08/091,458, filed Jul. 14, 1993, now abandoned, which was a continuation of U.S. patent application Ser. No. 07/936,854, filed Aug. 27, 1992, now abandoned, which was a continuation of U.S. patent application Ser. No. 07/662,928, filed Feb. 28, 1991, now U.S. Pat. No. 5,181,933.

BACKGROUND OF THE INVENTION

This invention relates to foot prostheses in general, and specifically to a split prosthetic foot which incorporates a plurality of curvilinear foot portions which cooperate with one another to provide the wearer with performance characteristics not available from prior art prostheses.

A number of prosthetic devices have attempted to provide energy-storing and -releasing functions to simulate ambulation on a natural limb. For example, see my U.S. Pat. No. 4,547,913 for my invention relating to a "Composite Prosthetic Foot and Leg", and U.S. Pat. No. 4,822,363 for my invention relating to a "Modular Composite Prosthetic Foot and Leg". Also, my pending applications Ser. Nos. 07/337,374, 07/585,920 and 07/293,824 disclose prosthetic foot devices with similar preferred materials and methods of manufacture, and with corresponding benefits therefrom.

Each of my aforementioned inventions is characterized by lightweight, elongated structures incorporating polymer impregnation of superimposed reinforcing laminae maintained in the desired configuration. Such configurations and constructions provide the desirable characteristics of strength and flexibility in the prosthetic member, and achieve a simulation of the performance of natural feet which had previously not been attainable. Such prostheses may be provided in modular assemblies, whereby the particular performance characteristics of a given prosthesis may be adapted and readily adjusted to meet the needs and activity level of the individual patient.

Other prosthetic foot devices include U.S. Pat. No. 3,335,428 to Gajdos, which attempts to duplicate the skeletal and skin structure of a natural human foot, U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

Although several of the aforementioned prostheses have provided flexure in a fore-and-aft direction, such prior art devices are relatively stiff and unresponsive with respect to torsional loading which might result from leaning to one side or from ambulation in a direction other than straight ahead. In fact, such prostheses provide a consistent energy response for loading at any given fore-and-aft location on the prosthesis, regardless of whether the loading occurs at one edge of the prosthesis or at the center thereof.

OBJECTS AND ADVANTAGES OF THE INVENTION

It is, therefore, an object of my invention to provide a prosthetic foot which provides a varying energy-absorbing and energy-storing performance dependent upon the lateral location of the contact between the foot and an underlying supporting surface, as well as the angle of impact therebetween. In particular, the prosthesis of my invention incorporates a plurality of foot portions capable of movement independently from one another.

In a preferred embodiment, as described below, the foot portions are fabricated by providing a slot through virtually the entire prosthesis, effectively dividing it into two independent prostheses. When both of these independent portions are similarly loaded and stressed, such as during straight-ahead walking, the portions cooperate and act in unison to achieve a performance similar to a foot with no division therein. When the prosthesis of my invention undergoes lateral loading, however, the various portions may act independently from one another and thereby provide performance characteristics which may vary substantially from those of a foot with no division therein.

In effect, the prosthesis of my invention simulates the sideways turning of a natural ankle, in that it permits the energy-storing structure of the entire foot to twist slightly from side to side in response to various loading conditions.

Moreover, such independent movement provides additional effective contact area between the bottom of the prosthesis and a confronting supporting surface, under the aforementioned lateral loading conditions. Instead of a single outer edge of the prosthesis contacting the supporting surface, two or more "edges" may achieve such contact, improving the traction or frictional interaction of the prosthesis on the surface.

Another object of my invention is the provision of a prosthetic foot of the aforementioned character which includes connecting or retaining means such as a strap for limiting the movement of the relevant independent foot portions, or selected ones of them, with respect to one another. This insures that the energy-storing capabilities of the entire foot are utilized when the foot is placed under conditions of extreme lateral stresses. In such situations, the connecting means effectively connects selected of the foot portions with a predetermined amount of play therebetween, whereby after one of the connected portions has been displaced that predetermined distance with respect to the other, the strap will require that both connected portions be simultaneously actuated in order for further displacement in that direction to occur.

It is a further object of my invention to provide a prosthetic foot of the aforementioned character which is of modular configuration, resulting in ready assembly and adjustability thereof. The foot of my invention preferably includes forefoot and heel portions that can be readily exchanged with correspondingly-constructed forefoot and heel portions to provide size adjustment or different spring rates to suit the size of foot of the amputee or the stride, height, weight, and activity level of the amputee. Therefore, a range of combinations of spring rate and size can be provided to the amputee, achieving a natural stride and resilience of gait.

Another object of the invention is the provision of a prosthetic foot of the aforementioned character in which the forefoot and heel portions of the prosthesis are fabricated from superimposed laminates maintained in operative relationship by an encapsulating polymer, and further in which said foot is susceptible to bending stress determined by the number of the laminates and polymers in the respective element. Thus, the laminates are encapsulated in a polymer and capable of spring stress response as loads are imposed thereupon during the utilization of said foot.

A further object of the invention is the provision of a prosthetic foot of the aforementioned character which consists of continuous, integrally and simultaneously formed attachment, ankle, arch and toe sections of a forefoot portion, and attachment and heel sections of a heel portion, said sections being respectively fabricated as unitary structures by polymer impregnation of superimposed reinforcing laminae maintained in the desired configuration of said foot and said sections being capable of spring stress generated energy storage whereby the subjection of the prosthetic foot to bending moments will cause uniform transmission of spring stress through said sections of said foot.

The polymers utilized to encapsulate the fibrous laminae are characterized by elasticity and flexibility so that the foot prosthesis deflects proportionally to the engagement of said prosthetic foot with an adjacent surface, causing the resultant energy to be stored and subsequently released when the gait of the amputee incorporating thrust and lift components results in the utilization of the stored energy and a consequent reduction of the energy expended by the amputee.

In order to impart a cosmetic aspect to the prosthetic foot, after proper fitting of the foot to insure that it is properly balanced and of appropriate size, the prosthesis may be encapsulated in a suitably shaped cosmetic shroud. The shroud must be sufficiently flexible so as not to inhibit the free movement and flexure of the foot, but, because of the inherently resilient and stress-absorbing characteristics of said foot, little dependence is needed upon the ancillary cushioning action of the shroud.

Other objects and advantages of the invention will be apparent from the following specification and the accompanying drawings, which are for the purpose of illustration only.

DESCRIPTION OF PREFERRED EMBODIMENT

Figure 4:
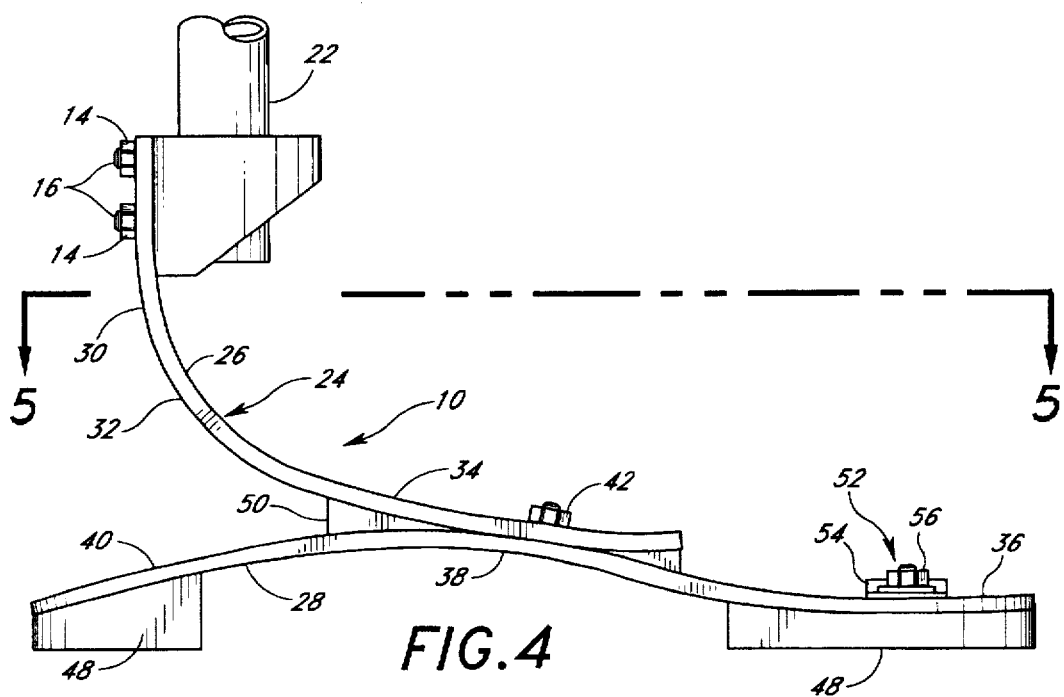
FIG. 4 is a partially cutaway side elevation sectional view, taken along line 4—4 of FIG. 1.
Figure 5:
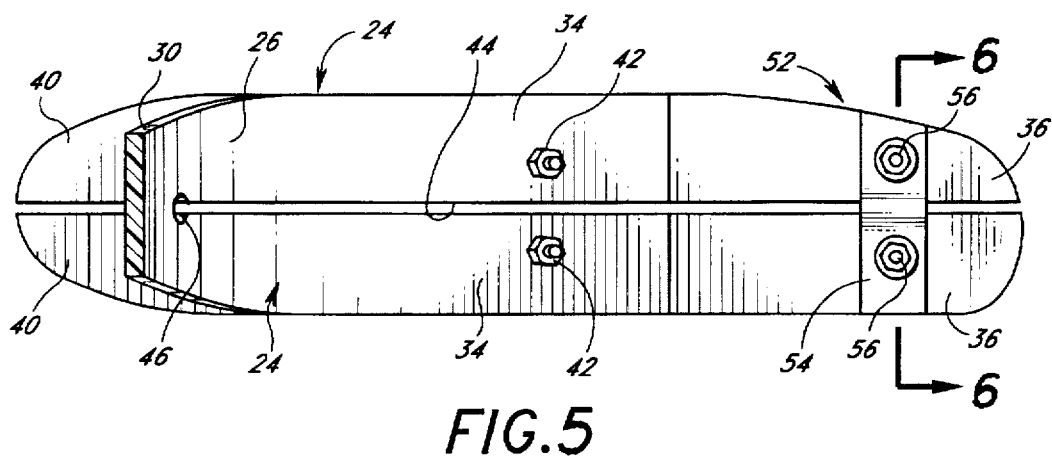
FIG. 5 is a partially sectional plan view of a prosthesis constructed in accordance with the teachings of the invention.
Figure 6:
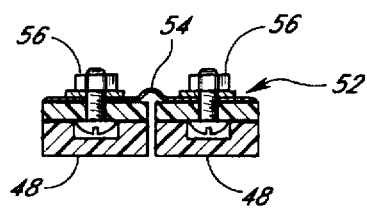
FIG. 6 is a sectional view, taken along line 6—6 of FIG. 5.

Referring to the drawings, and particularly to FIG. 4 thereof, I show a preferred embodiment of a foot prosthesis 10 constructed in accordance with the teachings of the invention and including attachment means 12 such as cooperating nuts 14, bolts 16, set screw 18, pylon 22 and coupling 20 for facilitating the operative engagement of the foot with a wearer's stump. Attached to the attachment means 12 and extending downwardly therefrom is a plurality of curvilinear foot portions 24, shown in the preferred embodiment as a bifurcated forefoot portion 26 and heel portions 28 secured thereto.

The foot portions 24 such as the preferred forefoot portion 26 further preferably include an attachment section 30, a curvilinear ankle section 32, FIG. 4, an arch section 34 and a toe section 36. The heel portions 28 preferably include an attachment section 38 and a heel section 40 projecting rearwardly therefrom. The various sections of the forefoot and heel portions, respectively, are preferably formed integrally with one another and simultaneously by the incorporation of a plurality of laminae embedded in a hardened, flexible polymer, similar to the fabrication methods taught in my above-noted patents.

The forefoot and heel portions of my invention, as well as the inventions of my above-noted patents, may also be manufactured by various other expedients, including injection molding and/or the use of thermoplastic materials and processes, or any of a range of combinations thereof.

Among other things, chopped fiber may be blended in a thermoplastic or thermoset resin and the resulting mixture injection molded into an appropriate configuration. Alternatively or additionally, thermoplastic laminae may be wound around an injection-molded core, or a thermoplastic resin may be injected between thermoplastic or thermoset laminae, whereby the laminates are bonded onto the injected material.

Figure 1:
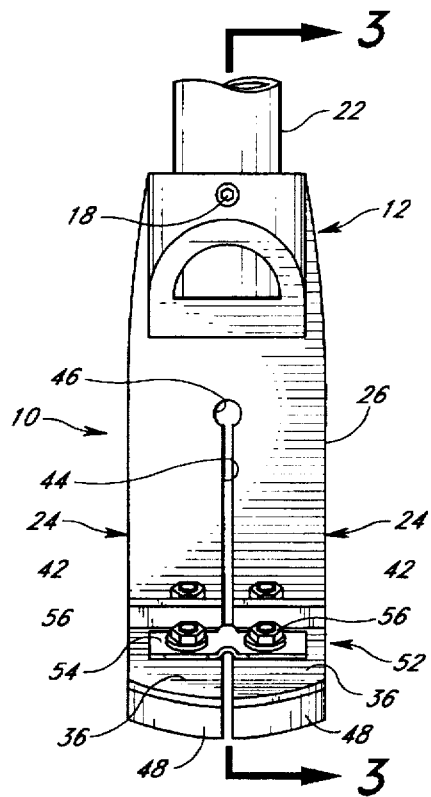
FIG. 1 is a front elevation view of a prosthesis constructed in accordance with the teachings of the invention.
Figure 2:
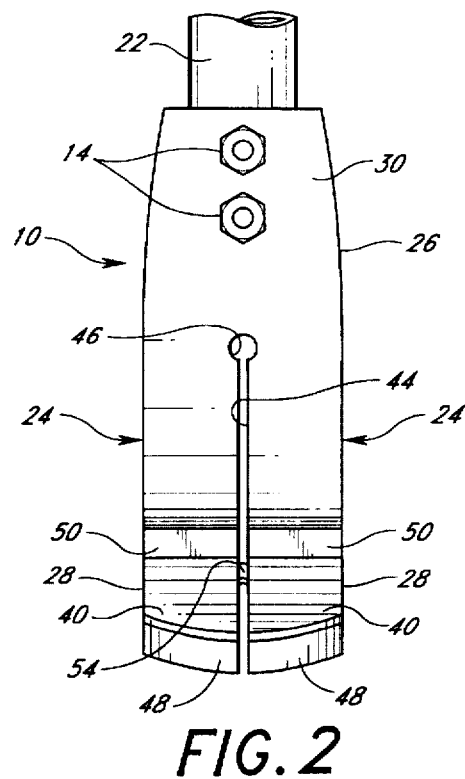
FIG. 2 is a rear elevation view of a prosthesis constructed in accordance with the teachings of the invention.
Figure 3:
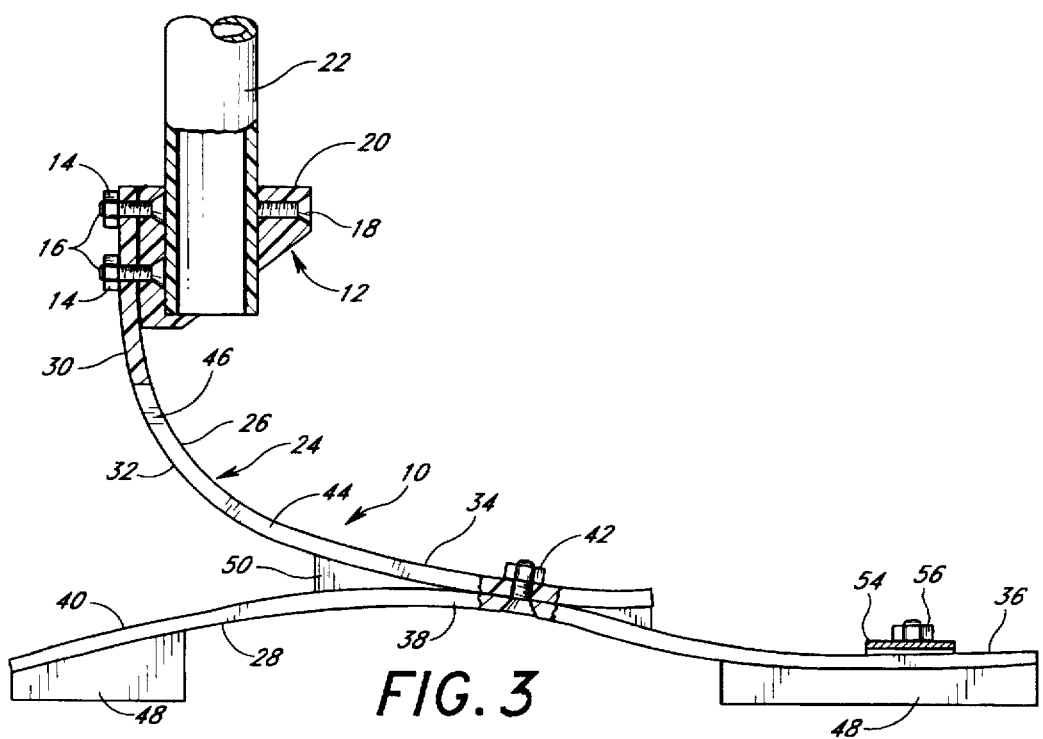
FIG. 3 is a side elevation view of a prosthesis constructed in accordance with the teachings of the invention.

The attachment section 38 of the heel portions 28 are preferably secured to corresponding intersections of the curvilinear ankle sections 32 and the arch sections 34 of the curvilinear foot portions 24. Such securement may be permanent, through simultaneous and integral fabrication or through the use of epoxy, glue or the like, or may be demountable, FIGS. 3 and 4, through the utilization of bolt, nut and washer combinations 42 assembled through corresponding holes in the forefoot and heel portions 26 and 28. Demountable attachment is preferred, in that it permits forefoot portions to be selectably matched with any of various heel portions having different spring rates, as more fully discussed below.

As indicated above, the forefoot and heel portions 26 and 28 are preferably fabricated from superimposed laminates maintained in operative relationship by an encapsulating polymer and susceptible to bending stress determined by the thickness of the laminates. The preferred materials and fabrication process are more thoroughly described and explained in my above-mentioned U.S. Pat. Nos. 4,547,913 and 4,822,363, and include laminates such as carbon fibers and/or fiberglass or synthetic fibers such as Kevlar. Exemplary alternative methods and materials are described hereinabove.

As illustrated in the accompanying Figures, the forefoot portion 26 is preferably bifurcated into two foot portions 24, although additional multiple portions 24 (not shown) may be beneficially provided and utilized without departing from the scope of my invention.

Figure 7:
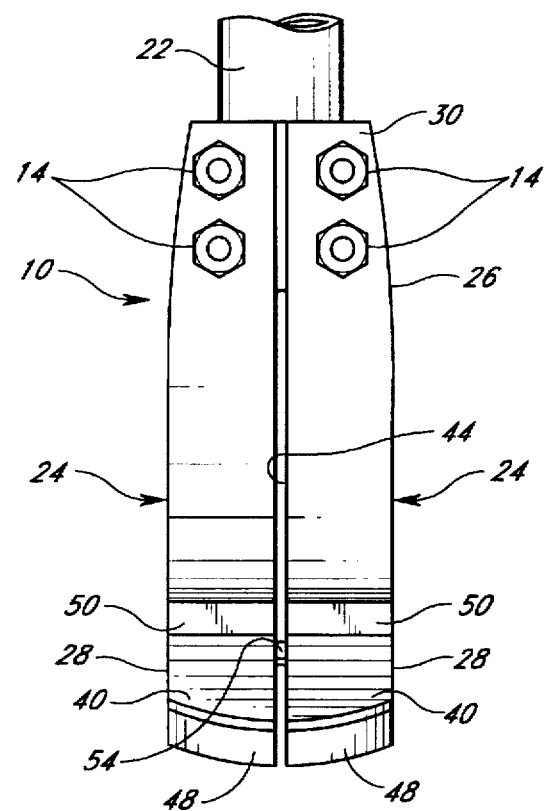
FIG. 7 is a rear elevation view of an alternative embodiment of a prosthesis constructed in accordance with the teachings of the invention.

Such bifurcation or further division may be accomplished through the incorporation of a slot 44 along the complete or substantially the complete length of the prosthesis 10. Such a slot 44 may be molded or subsequently cut into the prosthesis, or may be achieved by the juxtaposition of two or more completely separate foot portions 24 (as shown in FIG. 7), each of which would be operatively attached to the attachment means 12. If the slot 44 is molded or cut into a single forefoot portion 26, stress relief means 46, such as a hole, is preferably provided at the upper end of the slot 44, to prevent undesired excessive loading and deterioration of the prosthesis at that location.. Such a hole may be drilled or molded into the prosthesis 10.

The prosthesis of my invention is also preferably provided with underlying pads 48 and lever action blocks 50, as described in my aforementioned patents and pending applications. Such pad members may be affixed to the underside of the forefoot and heel portions, to create a profile for the bottom of the prosthesis 10 which corresponds to the interior of a shoe. Such a profile orients the foot 10, when the foot is in an unstressed state, at an appropriate angle for wearing shoes.

Additionally, the preferred embodiment of my invention includes retaining or connecting means 52 such as a strap 54 operatively attached to selected of the curvilinear foot portions 24 through the provision of nut, bolt and washer combinations 56 or the like. The strap 54 is preferably fabricated from impregnated canvas or other flexible, lightweight, tough material, and is located remote from the attachment section 30. By providing some play in the strap 54 rather than utilizing a taut strap, the selected foot portions 24 may flex independently of each other while exposed to lateral loading conditions, but will flex in a coordinated manner after sufficient movement has occurred to draw the strap taut. Thus, in extreme lateral loading conditions, more than one foot portion 24 will function to absorb and exert energy and prevent overload of a single foot portion 24.

It will be obvious to those skilled in the art that a virtually infinite variety of forefoot portions 26 and heel portions 28 may be fabricated, each having unique spring stress response characteristics determined by the configuration, composition and amount of the various component materials utilized therein. The aforementioned demountable connection of the heel portion to the forefoot portion therefore permits interchangeability of those portions to match the weight, stride and activity schedule of the wearer utilizing the prosthetic foot.

Those skilled in the art will understand that attachment means 12 have been described hereinabove merely by way of example, and that many alternative attachment means are available and may be utilized without departing from the scope of the invention.

The attachment section or sections 30, when assembled with the attachment means 12, are substantially rigid and capable of sustaining torsional, impact, and other loads impressed thereupon by the wearer during use of the foot 10. In addition, the inherent rigidity of the attachment section or sections prevents them from being distorted in any way and causes the effective transmission of the aforesaid loads imposed thereupon between the wearer and the prosthetic foot 10.

The forefoot and heel portions 26 and 28 can be provided with different numbers of laminates to make them more or less compliant to loads transmitted between the wearer and surface upon which the foot 10 is impacting. Consequently, when confronted with various anomalies in an amputee, such as an overweight condition or excess activity levels, the structure of the forefoot and heel portions can be materially modified to provide action which is precisely adjusted to the needs of the amputee. Moreover, a variety of forefoot and heel portions 26 and 28 can be made available to an amputee, allowing the flexibility of the prosthesis to be adjusted on the basis of the particular activity which the amputee is undertaking.

Those skilled in the art will understand that auxiliary flexure members (not shown) such as those described and shown in my co-pending application Ser. Nos. 07/293,824 (see FIG. 7 therein) and 07/337,374 may be efficaciously utilized in connection with any embodiment of the above-described invention, without departing from the scope of the teachings hereof.

In the preferred embodiment, the forefoot and heel portions 26 and 28 are constructed with some slight tapering of thickness along the length thereof, although those skilled in the art will understand that the invention is not limited to such tapering construction.

The materials from which the portions 26 and 28 are fabricated are preferably such as to provide an energy-storing, resilient, spring-like effect. This is because each engagement of the prosthetic foot 10 with an adjacent surface impresses compression, torsional, and other loads upon the prosthesis which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The multi-portioned prosthesis of my invention thus provides a compliance to lateral stresses and loading not previously achievable, and accomplishes this desirable result in a light-weight and responsive prosthesis. Moreover, the modularity of the invention permits the performance characteristics of the prosthesis to be fine-tuned and adjusted to the particular weight, size, and activity of the wearer.

As previously mentioned, the attachment section 30, the ankle section 32, the arch section 34, and the toe section 36 of the forefoot portion 26 are preferably formed integrally. Likewise, the attachment section 38 and the heel section 40 of the heel portion 28 are preferably formed integrally. The configuration of these sections is the means whereby bending and compressive loads imposed during impingement of the prosthetic foot 10 upon an adjacent surface are absorbed and subsequently reimposed upon said surface. These various sections are so designed that they function, substantially, to permit some flexure of the portions 26 and 28. In combination with the multiple foot portions 24, the prosthesis 10 functions in a manner analogous to a normal foot and normal ankle joint, permitting the wearer to experience a more natural gait and feel with the prosthesis than was possible with prior art prostheses.

The prosthetic foot of my invention can thus be provided in different sizes to correspond to the size of the natural foot of the wearer of the prosthesis 10. When such different sizes are provided, corresponding reduction or increase in the number of laminae and thickness of taper, if any, of the respective sections of the forefoot and heel portions 12 and 14 can be made to provide for the proper flexure of said sections.

Moreover, the flexibility of the prosthetic foot of my invention may be further increased, while still maintaining acceptable strength characteristics, by providing an auxiliary ankle member or an auxiliary forefoot portion (not shown, but similar to that illustrated in my co-pending application Ser. No. 07/337,374). Such an auxiliary member or portion would be operatively affixed to the forefoot portions 26 to provide some relative movement therebetween.

The aforementioned flexure of the various foot portions 24 provides the capacity for increased surface area contact between the bottom of the prosthesis 10 and a confronting supporting surface during both the impact and delivery phases of lateral loading of the prosthesis 10. Instead of a single edge of the prosthesis effectively contacting the supporting surface, the above-described independent flexure of the portions 24 permits corresponding edges of each such portion 24 to contact the supporting surface, thereby improving the traction or frictional contact between the bottom of the prosthesis and the confronting surface.

The prosthesis of my invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

I claim:

1. A foot prosthesis configured to be secured to a socket or pylon for supporting an amputee relative to a support surface, said foot prosthesis comprising:

an upper attachment section configured to secure said foot prosthesis to said socket or pylon; and a plurality of longitudinal foot sections attached to said upper attachment section and including at least two unsecured ends terminating anteriorly with respect to a vertical centerline of said socket or pylon so as to be adjacent said support surface during a stance phase and at least two unsecured ends terminating posteriorly with respect to a vertical centerline of said socket or pylon so as to be adjacent said support surface during a stance phase for providing support for said amputee during normal walking or running activities, each of said longitudinal foot sections being disposed in a spaced apart manner with respect to at least one other longitudinal foot section and separated from one another substantially completely along their length such that each of said longitudinal foot sections can flex substantially independently of one another substantially completely along its length so as to provide resilient inversion and eversion support to said amputee.

2. The foot prosthesis of claim 1, wherein one or more slots separate said longitudinal foot sections along substantially the entire length of said foot sections.

3. The foot prosthesis of claim 2, wherein said one or more slots are formed by cutting away portions of a single support member so as to define said longitudinal foot sections.

4. The foot prosthesis of claim 2, wherein said one or more slots are formed by the juxtaposition of two or more completely separate longitudinal foot sections each of which is operatively and demountably attached to said upper attachment section.

5. The foot prosthesis of claim 1, wherein at least two of said foot sections terminate in a toe end, and a strap is secured to said longitudinal foot sections proximate said toe end, said strap being configured to limit the independent movement of said longitudinal foot sections beyond a predetermined desired range.

6. The foot prosthesis of claim 1, wherein at least two of said longitudinal foot sections terminate in a heel end, said foot sections being fabricated from superimposed laminates maintained in operative relationship by an encapsulating polymer.

7. The foot prosthesis of claim 1, wherein said upper attachment section is configured to secure said foot prosthesis to a tubular pylon member.

8. The foot prosthesis of claim 1, wherein said foot prosthesis is configured to be secured to said socket or pylon by at least one nut and bolt member.

9. The foot prosthesis of claim 1, wherein at least two of said longitudinal foot sections comprise forefoot members demountably secured to said upper attachment section whereby they can be readily replaced with similar forefoot members having different size or spring rate characteristics to suit the size, stride, height, weight and/or activity level of the amputee.

10. A foot prosthesis having a length and configured to be secured to a socket or pylon for supporting an amputee relative to a support surface, said foot prosthesis comprising:

an upper attachment section configured to secure said foot prosthesis to said socket or pylon;

a plurality of foot members extending downward from said upper attachment section and having at least two unsecured ends terminating substantially anteriorly so as to be adjacent said support surface during a stance phase for resiliently supporting said amputee during normal walking or running activities, said foot members being substantially spaced apart from at least one other foot member by a slot extending along substantially the entire length of said foot prosthesis whereby said foot members independently flex substantially completely along their length such that resilient inversion and eversion support is thereby provided.

11. The foot prosthesis of claim 10, wherein at least two of said foot members comprise an ankle section, a toe section and a heel section and wherein a strap interconnects said foot members proximate said toe sections for limiting the independent flexing of said foot members beyond a predetermined desired range.

12. The foot prosthesis of claim 10, wherein said foot members are substantially symmetric with one another about the sagittal plane of said foot prosthesis.

13. The foot prosthesis of claim 10, wherein right and left foot members comprise sheet-like members that are bent or curved.

14. The foot prosthesis of claim 13, wherein said foot members are substantially curvilinear and define an ankle section, a toe section and a heel section of said foot prosthesis.

15. The foot prosthesis of claim 10, wherein at least two of said foot members comprise heel sections extending posteriorly so as to be adjacent said support surface during a stance phase, said heel sections being fabricated from superimposed laminates maintained in operative relationship by an encapsulating polymer.

16. The foot prosthesis of claim 10, wherein at least two of said foot members comprise an ankle section, a toe section and a heel section and wherein said heel sections are demountably secured to said corresponding ankle sections or toe sections such that various heel sections having different spring characteristics can be interchanged.

17. The foot prosthesis of claim 10, wherein said one or more slots are formed by cutting away portions of a single support member so as to define said foot members.

18. The foot prosthesis of claim 10, wherein said one or more slots are formed by the juxtaposition of two or more completely separate foot members each of which is operatively and demountably attached to said upper attachment section.

19. The foot prosthesis of claim 10, wherein at least two of said foot members comprise forefoot members demountably secured to said upper attachment section whereby they can be readily replaced with similar forefoot members having different size or spring rate characteristics to suit the size, stride, height, weight and/or activity level of the amputee.

20. A foot prosthesis configured to be secured to a socket or pylon for supporting an amputee relative to a support surface, said foot prosthesis comprising:

an upper attachment section configured to secure said foot prosthesis to said socket or pylon; and a foot portion attached to said upper attachment section, said foot portion including an ankle section, a toe section and a heel section, said foot portion comprising a plurality of independently formed and demountable foot sections spaced apart from at least one other foot section substantially completely along their length and having unsecured ends at least two of which terminate anteriorly with respect to a vertical centerline of said socket or pylon so as to be adjacent said support surface during a stance phase and at least two of which terminate posteriorly with respect to a vertical centerline of said socket or pylon so as to be adjacent said support surface during a stance phase, said foot sections being adapted to independently flex so that said foot prosthesis provides varying energy-absorbing and energy-storing performance dependent upon the terrain of said support surface and the angle of impact of said foot prosthesis;

whereby multi-point independent foot suspension and resilient inversion and eversion support is thereby provided.

21. A foot prosthesis comprising:

a plurality of anterior support members each having at least a portion thereof configured to extend substantially anteriorly toward a support surface during a stance phase and being spaced apart from one another substantially completely along the length of said portion such that each of said anterior support members has at least one substantially unsecured end sized and configured to independently flex while maintaining contact with said support surface; and a plurality of posterior support members each having at least a portion thereof configured to extend substantially posteriorly toward said support surface during a stance phase and being spaced apart from one another substantially completely along the length of said portion such that each of said posterior support members has at least one substantially unsecured end sized and configured to independently flex while maintaining contact with said support surface;

whereby multi-point independent foot suspension is provided for accommodating uneven or angled terrain by individually flexing to conform to the terrain.

22. The foot prosthesis of claim 21, wherein said anterior support members are spaced apart from one another by one or more gaps extending between said anterior support members along substantially the entire length thereof.

23. The foot prosthesis of claim 21, wherein said posterior support members are spaced apart from one another by one or more gaps extending between said posterior support members along substantially the entire length thereof.

24. The foot prosthesis of claim 21, wherein at least two of said anterior support members terminate in a toe end, and a strap is secured to said anterior support members proximate said toe end, said strap being configured to limit the independent movement of said anterior support members beyond a predetermined desired range.

25. The foot prosthesis of claim 21, wherein at least two of said anterior or posterior support members are demountably secured such that they can be readily replaced with similar support members having different size or spring rate characteristics in order to suit the size, stride, height, weight and/or activity level of the amputee.

26. The foot prosthesis of claim 21, wherein at least two of said anterior and/or posterior support members are substantially symmetric with one another about the sagittal plane of said foot prosthesis.

27. The foot prosthesis of claim 21, wherein at least two of said anterior and/or posterior support members comprise sheet-like members that are bent or curved.

28. A prosthetic foot having multi-point independent foot suspension comprising:

an attachment section sized and configured to attach said prosthetic foot to a socket or leg prosthesis;

a plurality of anterior suspension members each having a substantially unsecured end terminating substantially anteriorly of said attachment section so as to be adjacent a support surface during a stance phase and being sized and configured so as to independently flex while maintaining contact with said support surface; and a plurality of posterior suspension members each having a substantially unsecured end terminating substantially posteriorly of said attachment section so as to be adjacent said support surface during a stance phase and being sized and configured so as to independently flex while maintaining contact with said support surface;

whereby said suspension members independently flex to accommodate uneven or angled terrain.

29. The prosthetic foot of claim 28, wherein at least two of said anterior suspension members are spaced apart from one another by one or more gaps extending between said anterior suspension members along substantially the entire length thereof.

30. The prosthetic foot of claim 28, wherein at least two of said posterior suspension members are spaced apart from one another by one or more gaps extending between said posterior suspension members along substantially the entire length thereof.

31. The prosthetic foot of claim 28, wherein at least two of said anterior suspension members terminate in a toe end, and a strap is secured to said anterior suspension members proximate said toe end, said strap being configured to limit the independent movement of said anterior suspension members beyond a predetermined desired range.

32. The prosthetic foot of claim 28, wherein at least two of said anterior or posterior suspension members are demountably secured such that they can be readily replaced with similar suspension members having different size or spring rate characteristics in order to suit the size, stride, height, weight and/or activity level of the amputee.

33. The prosthetic foot of claim 28, wherein at least two of said anterior and/or posterior suspension members are substantially symmetric with one another about the sagittal plane of said foot prosthesis.

34. The prosthetic foot of claim 28, wherein at least two of said anterior and/or posterior suspension members comprise sheet-like members that are bent or curved.

* * * * *